US005629156A

United States Patent [19]
Shah et al.

[11] Patent Number: 5,629,156
[45] Date of Patent: May 13, 1997

[54] MULTIPLE CAPTURE PROBE SANDWICH ASSAYS

[75] Inventors: Jyotsna Shah, Nashua, N.H.; Walter King, Andover, Mass.; Jing Liu, Waltham, Mass.; James Smith, Shrewsbury, Mass.; Eugene Serpe, Winston-Salem, N.C.; Sonya Popoff, Wayland, Mass.

[73] Assignee: Amoco Corporation, Chicago, Ill.

[21] Appl. No.: 366,422

[22] Filed: Dec. 29, 1994

Related U.S. Application Data

[63] Continuation of Ser. No. 959,939, Oct. 9, 1992, abandoned.
[51] Int. Cl.$^6$ .............................. C12Q 1/68; C12P 19/34
[52] U.S. Cl. .................................. 435/6; 435/91.2
[58] Field of Search ...................... 435/6, 91.2, 91.21, 435/91.51

[56] References Cited

U.S. PATENT DOCUMENTS 5,015,569  5/1991  Pontius ........................................ 435/6

FOREIGN PATENT DOCUMENTS 9010716  9/1990  WIPO ............................... C12Q 1/68

OTHER PUBLICATIONS

Pritchard et al. Amplified detection of viral nucleic acid at subattomole levels using Q beta replicase. Ann. Biol. Clin. (Paris) (1990) 48:492–497. Abstract. 1988.

Stratagene Catalog, p. 39.

Morrissey, D.V. et al. Nucleic Acid Hybridization Assays Employing dA–Tailed Capture Probes I. Multiple Capture Methods. Anal. Biochem. (1989) 181: 345–359.

*Primary Examiner*—Kenneth R. Horlick
*Assistant Examiner*—Joyce Tung
*Attorney, Agent, or Firm*—Norval B. Galloway

[57] ABSTRACT

New methods for performing sandwich assays have been discovered. The assays utilize dual capture probes and eliminate noise resulting from nonspecific binding of detector probe to capture probe.

9 Claims, 3 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: NO     ( x i ) SEQUENCE DESCRIPTION: SEQ ID NO:1:

CCTTTAACGT TACTCGGATG CCCAAA      26

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: NO     ( x i ) SEQUENCE DESCRIPTION: SEQ ID NO:2:

CTTTAACGTT ACTCGGATGC CCAAATATCG CCACAT      36

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: NO     ( x i ) SEQUENCE DESCRIPTION: SEQ ID NO:3:

CTGCTGCCTC CCGTAGGAGT TTGGGCCGTG TCTCAGTTCC AGTGT      45

( 2 ) INFORMATION FOR SEQ ID NO:4:

( i ) SEQUENCE CHARACTERISTICS:
        ( A ) LENGTH: 280 base pairs
        ( B ) TYPE: nucleic acid
        ( C ) STRANDEDNESS: single
        ( D ) TOPOLOGY: linear     ( i i i ) HYPOTHETICAL: NO     ( i v ) ANTI-SENSE: NO     ( x i ) SEQUENCE DESCRIPTION: SEQ ID NO:4:

```
GGGGACCCCC  CCGGAAGGGG  GGGACGAGGU  GCGGGGACCU  CGUACGGGAG  UUCGACCGUG    60

ACGCGUCGUC  GAGUUGAGGC  CUUUACCCCA  CCAACUAGCU  GAUAUCACAU  ACUGAAUCUU   120

UAGUCACGGG  CUAGCGCUUU  CGCGCUCUCC  CAGGUGACGC  CUCGUGAAGA  GGCGUGACCU   180

UCGUGCGUUU  CGGUAACGCA  CGAGAACCGC  CACGCUGCUU  CGCAGCGUGG  CCCCUUCGCG   240

CAGCCCGCUG  CGCGAGGUGA  CCCCCCGAAG  GGGGGUUCCC                           280
```

MULTIPLE CAPTURE PROBE SANDWICH ASSAYS

This is a continuation of application Ser. No. 07/959,939 filed on Oct. 9, 1992, abandoned.

FIELD OF THE INVENTION

The invention relates to methods and kits for detecting target molecules in samples. In particular, the target molecules can be nucleic acid fragments from clinical samples. Embodiments of the invention provide methods for rapid and sensitive detection of target nucleic acids.

BACKGROUND

The utility of detecting target nucleic acid sequences in clinical diagnostics is well established. Various methodologies have been developed for detecting particular target nucleic acid sequences as diagnostic of the presence of the target organism. These include hybridization assays which rely upon one or more tailored nucleic acid probes which are able to hybridize or bind to sequences of nucleic acid within the target nucleic acid.

The hybridization assays developed to date remain limited due to the presence of artificial signal or noise generated during the assay and competitive with the signal generated by captured target nucleic acid. For example, sandwich hybridization assays have been developed which employ two separate nucleic acid probes able to hybridize to mutually exclusive nucleic acid sequences within the target nucleic acid. One of the probes, the detector probe, is constructed to carry a detectable label moiety to permit detection of the captured target. The second probe, the capture probe, is constructed to permit binding to a support as well as the target to facilitate sample purification and isolation of the captured target. Under hybridization or binding conditions, the two probes hybridize with the target nucleic acid to form a capture probe:target:detector probe ternary complex. Introduction of the support under binding conditions results in capture of the ternary complex by the support. The detector probe can then be isolated and measured to determine the presence or quantity of target in the sample.

The sensitivity of such sandwich hybridization assays is known to be limited, however, because the detector probe will bind to the assay support directly notwithstanding the absence of target in the sample. The binding of detector probe directly to support in the absence of target is referred to as nonspecific binding. Additionally, the sample to be assayed may also have other nucleic acid sequences of some similarity to the sequence selected as the target, known as pseudo targets. These pseudo targets, at high levels associated with detector probe, may also bind nonspecifically to the assay support and, further, bind to the detector probe thereby binding the detector probe to the support in the absence of target and creating noise. In addition, pseudo target associated with detector probe can hybridize with a few mismatches to the capture probe and, thus, be captured on the assay support. This binding of detector probe to support through a nucleic acid sequence similar to the target is referred to as nonspecific hybridization. Nonspecific binding and nonspecific hybridization generate detectable signal or noise which is cumulative with the signal generated by capture of the ternary complex and target. The problem of noise due to nonspecific binding and nonspecific hybridization is often exacerbated by the presence of excess detector probe in the assay to facilitate rapid and complete formation of the target:detector probe hybridization.

Conventional sandwich hybridization assays are able to detect to a limit of about $10^8$ targets. However, diagnostic assays often seek to detect the presence of targets present in samples at concentrations much lower than the $10^8$ target threshold presently permitted by conventional assays. Researchers have attempted to eliminate or, at least, lessen the noise from sandwich hybridization assays. One method, hereafter referred to as Reversible Target Capture or RTC, has been effective in reducing such background noise. Reversible Target Capture involves cycles of capture and release of the ternary complex from a succession of supports.

Initially, following conventional sample preparation to expose the target nucleic acid for detection, capture and detector probes are added to the sample medium. In the presence of target and upon imposition of binding conditions the ternary complex is formed. Upon introduction of a suitable support, the ternary complex is captured by the support. However, a certain amount of detector probe binds nonspecifically to the support. The support and bound ternary complex are then removed from the sample medium, typically washed, and then introduced to a second sample medium. Releasing conditions are then imposed causing the ternary complex to be released from the support. The original support is then removed from the second sample medium, thereby removing some of the nonspecifically bound detector probe from the assay.

Thereafter, a second support is introduced to the second sample medium, binding conditions again imposed and the ternary target containing complex is again captured. Since some of the detector probe nonspecifically bound to the original support may also have been released into the second sample medium by imposition of releasing conditions and, thus, be available for nonspecific binding to the second support, additional cycles of release and capture may be necessary to achieve maximal sensitivity for the assay. Typically, three cycles of target capture are sufficient to reduce noise below detectable limits in a conventional sandwich hybridization assay format. Reversible Target Capture and other methods aimed at reducing noise resulting from nonspecific binding of the detector probe are described in detail in European Patent Application No. 87309308.2 (Publication No. 0265244), Analytical Biochemistry, 181, 345–359 (1989), and Analytical Biochemistry, 181, 360–370 (1989). All are hereby incorporated by reference.

Sandwich hybridization assays supplemented with Reversible Target Capture are able to extend the level of sensitivity to about $10^6$ targets. Notwithstanding the success of these techniques, however, those in the art have continued to look for additional ways to enhance the sensitivity of the assay. These include the use of amplification schemes to further amplify the target or signal generated by the assay. For example, European Patent Application No. 88312135.2 (Publication No. 0328829) describes improved assay methods which amplify the target polynucleotide before detecting it. Amplification is accomplished enzymatically using polymerase enzymes. For example, target DNA and the enzyme core RNA polymerase can be used to form RNA complements to the target DNA. The RNA complements are then detected. Similarly, target RNA can be replicated by enzymes such as Qβ-replicase and reverse transcriptase before detection. These techniques are fully compatible with Reversible Target Capture and can be used to enhance assay sensitivity to approximately $10^6$ targets. These techniques are described more fully in European Patent Application No. 88312135.2 which is incorporated herein by reference.

Alternatively, assay sensitivity can be enhanced by amplifying the signal produced by the detector probe or, more particularly, the detector probe itself. This can be accomplished by adopting midivariant (MDV-1) RNAs for use as detector probes. Midivariant-like RNAs can serve as templates for Qβ-replicase and can be replicated thereby. Hence, detector probes can be constructed for amplification by Qβ-replicase to further enhance the assay. The use of Qβ-replicase amplification in nucleic acid sandwich hybridization assays to enhance assay sensitivity to approximate by $10^6$ targets is described by Cahill et at., Clinical Chemistry, 37,1482(1991) which is incorporated herein by reference.

Notwithstanding the advances made to date, the sensitivity of nucleic acid sandwich hybridization assays remains limited by background noise generated during the assay. Hence, it would be beneficial to increase assay sensitivity to a point where the sensitivity of the assay is limited by the ability of the assay to detect signal from the target only, and not by background noise produced during the assay. Accordingly, it is, an object of the present invention to provide a sandwich hybridization assay of enhanced sensitivity. It is another object of the present invention to provide a sandwich hybridization assay for which the sensitivity of the assay is limited by the signal generated by target and not by background noise generated during the assay.

SUMMARY OF THE INVENTION

It has now been discovered that significantly more sensitive sandwich hybridization assays obtain when certain modifications are made to the Reversible Target Capture assay method. The sensitivity of the new assays is limited by the signal generated as a result of detected target and not by background noise. Introduction of the new assay methods into a hybridization assay utilizing a signal amplification scheme such as using Qβ-replicase to replicate an RNA-like template within the detector probe permits the sensitivity of the assay to be enhanced by a factor of $10^3$. Thus, sensitivity can be increased by up to three orders of magnitude.

Previous efforts aimed at reducing background noise in sandwich hybridization assays have been directed to reducing the noise resulting from the nonspecific binding of labeled detector probe to the supports used in the assay. Although techniques such as Reversible Target Capture are effective in reducing such noise, residual noise remained in the assay. It has now been discovered that this residual noise can be reduced significantly to the point where it is eliminated entirely. It has been discovered that this residual noise can be eliminated by using two or more separate capture probes and modifications of the RTC format.

It is believed the new assay formats eliminate noise due to nonspecific binding of the detector probe to the capture probe. Prior Reversible Target Capture methods utilized a single capture probe and preserved the capture probe:target-:detector probe ternary complex throughout the assay. Accordingly, detector probe nonspecifically bound to the capture probe is maintained throughout the target release and recapture cycles of RTC and is present at the end of the assay to generate noise in competition with the signal resulting from the captured target. This noise which remains in the assay during target release and recapture is termed cyclable noise. The methods described herein are effective at removing cyclable noise as well as the noise resulting from nonspecific binding of detector probe to support. In effect, the methods can produce a sandwich hybridization assay entirely free of background noise.

The invention comprises two classes of Dual Capture assays. The Class I method comprises the steps of contacting the sample with a first capture probe and detector probe which in the presence of target bind to the target to form a first capture probe:target:detector probe ternary complex; separating the target:detector probe segment of the ternary complex from the first capture probe; contacting the sample with a second capture probe which binds to the target to form a second capture probe:target:detector probe ternary complex; minimizing the amount of detector probe nonspecifically bound to the second capture probe; and monitoring the second ternary complex for the presence or absence of detector probe.

The Class II method comprises the steps of contacting the sample with a first probe and a second capture probe which in the presence of target bind to the target to form a target complex; minimizing the amount of second capture probe present in the sample; contacting the sample with detector probe and fresh first capture probe which in the presence of target binds to the target forming a quaternary complex comprising a second target complex of the second capture probe:target:detector probe and bound first capture probe; minimizing the amount of detector probe bound to the second capture probe of the second target complex; and monitoring the second target complex for the presence or absence of detector probe.

More particularly, a preferred embodiment of the Class I method of the invention comprises the steps of contacting the sample medium to be assayed for target with a first capture probe and detector probe which, in the presence of target, bind to the target to form a first ternary complex of first capture probe:target:detector probe; contacting the sample with a first support wherein the first support bind: to the first capture probe thereby binding the first ternary complex to the support; substantially separating the first support and first ternary complex from the sample medium; introducing the first support and first ternary complex to a second medium and releasing the target:detector probe segment of the first ternary complex from the first support and capture probe; substantially separating the first support and capture probe from the second medium; introducing a second support and second capture probe to the second medium to form a second ternary complex of second capture probe: target:detector probe bound to the second support; substantially separating the second support and second ternary complex from the second medium; introducing the second support and second ternary complex to a third medium and releasing the second ternary complex from the second support; substantially separating the second support from the third medium; and detecting the presence of target in the third medium. Additional cycles of target capture and release can be performed as necessary to complete the reduction of noise due to nonspecific binding of detector probe to support.

A preferred embodiment of the Class II method comprises the steps of contacting the sample to be assayed with a first capture probe and a second capture probe wherein the first and second capture probes bind to the target to form a target complex; contacting the sample with a second support which binds to the second capture probe thereby binding the target complex to the second support; substantially separating the second support and bound target complex from the sample; introducing the second support and bound target complex into a second medium and releasing the target complex from the second support; substantially separating the second support from the second medium; contacting the second medium with a first support which binds to the first capture probe thereby binding the target complex; substantially separating the first support and bound target complex from the second medium; introducing the first support and bound target complex into a third medium and releasing the second capture probe: target segment of the target complex from the first support and first capture probe; substantially separating the first support and first capture probe from the third medium; contacting the third medium with detector probe and fresh first capture probe which in the presence of target bind to the target to form a quaternary complex comprising a second target complex of the second capture probe:target::detector probe and bound first capture probe; contacting the third medium with fresh first support which binds with the first capture probe to bind the quaternary complex; substantially separating the first support and bound quaternary complex from the third medium; introducing the first support and bound quaternary complex into a fourth medium and releasing the second target complex from the first support and first capture probe; substantially separating the first support and bound first capture probe from the fourth medium; contacting the fourth medium with second support which binds to the second capture probe; substantially separating the second support and bound second target complex from the fourth medium; introducing the second support and bound second target complex into a fifth medium and releasing the second target complex from the second support; substantially separating the second support from the fifth medium; and monitoring the second target complex for the presence or absence of detector probe.

DETAILED DESCRIPTION OF THE INVENTION

It has now been discovered that the sensitivity of sandwich assays can be enhanced considerably using assay methods which are modifications of conventional sandwich assays using the Reversible Target Capture technique described, for example, in European Patent Application No. 873093082. The methods disclosed here substantially eliminate the background noise that would otherwise accrue during the assay and, thus, limit the sensitivity of the assay. In doing so, the methods disclosed here extend the sensitivity of the assays by up to three orders of magnitude and result in assays with sensitivity limited by true signal response rather than noise.

The methods of the invention are compatible with sandwich assays generally. They are particularly advantageous in sandwich hybridization assays for nucleic acid targets. The methods are also amenable to kits, automation and instrumentation. Thus, the methods disclosed herein permit rapid, convenient and sensitive sandwich assays for conventional assay targets.

The assay methods disclosed herein are advantageous because they address a heretofore unappreciated noise component of the sandwich assay. Previously, assay methods had been developed to reduce noise resulting from nonspecific binding of detector probes to supports used in sandwich assays and to materials in the sample which are somewhat similar to the actual target. In nucleic acid hybridization assays, these can be nucleic acid sequences which bear some similarity to the targets.

The assay methods of the invention are generally termed Dual Capture Class I and Class II assays. In contrast to conventional sandwich assays which utilize a single capture probe throughout the assay, the Dual Capture assays use multiple capture probes in the assay. Moreover, although it is necessary that the capture probes be able to bind to both the supports and targets used in the assay, it is also a feature of the invention that the capture probes are constructed and selected for use in the assay such that some bind more strongly to the assay support than the target and so can be separated from the target while remaining bound to the support, while others bind more strongly to the target than the support and so can be separated from the support while remaining bound to the target.

For example, in the Dual Capture Class I assay, the capture probes may bind to the same or different regions of the target but are also constructed such that the first capture probe is more readily separated from the target than the support to which it binds while the second capture probe is more readily separated from the support than the target. Initially, the first capture probe and detector probe are contacted with the sample and allowed to bind with the target to form a first ternary complex. Next, a first support which binds to the first capture probe is contacted with the sample. The target and detector probe are then captured through the first capture probe to the support. The first support and bound first ternary complex are substantially separated from the sample medium and introduced to a second medium. Thereafter, the target and detector probe segment of the ternary complex is released and separated from the first capture probe and support which are then removed from the second medium. Presumably, removal of the support and first capture probe removes detector probe nonspecifically bound to the support and to the capture probe, thereby removing background noise from the assay.

Next, the target and detector probe can be recaptured by first introducing the second capture probe to form a second ternary complex and then a second support to the second sample medium. Thereafter, the second support and second ternary capture probe: target:detector probe complex can be transferred to a third medium for processing. Then the second support can be separated from the second ternary complex and separated from the third medium. The ternary complex is then monitored for the presence or absence of detector probe. When target is present in the original sample, detector probe will be detected. Presumably, separation of the second support from the third medium removes detector probe nonspecifically bound to the second support.

The capture and release using first and second capture probes can be performed in either order. Moreover, additional cycles of capture and release using either capture probe or still another capture probe can be performed to further reduce background noise as needed. As illustrated in Example 1, one cycle using the first capture probe and two cycles using the second capture probe eliminate almost all of the background noise.

Similarly, the Dual Capture Class II method also uses separate capture probes to remove background noise. In this method, the separate capture probes bind to separate regions of the target. The separate capture probes are again constructed such that one will bind more strongly to a support than the target while the other will bind more strongly to the target than support. Moreover, the capture probes and supports are selected so that there is minimal cross reactivity between them. The first capture probe and fast support are selected so as to have minimal affinity for the second support and second capture probe, respectively.

In the Class II method, both capture probes are bound to the target to begin the assay. One of the capture probes will be used for target capture and release cycling in completion of the assay. Accordingly, steps are taken to minimize the amount of any excess of this capture probe from the assay, i.e., any capture probe not specifically bound to the target, before introduction of the detector probe into the assay.

For example, the first and second capture probes are combined with the target and bind thereto to form a target complex. Excess first capture probe not bound to the target can be removed by capturing the target complex with a second support specific for the second capture probe but which has no affinity for the first capture probe. The second support and captured target complex can be separated from the sample medium and transferred to a second medium for further processing. The second capture probe is constructed to bind more strongly to the target than the second support. Thus, the target complex can then be separated from the second support. The second suport can be separated from the second medium.

Thereafter, the target complex can be captured with a first support specific for the first capture probe. This first capture probe is constructed to bind more strongly to the first support than to the target. Thus, the first support and captured target complex can be separated from the second medium and introduced into a third medium for further processing. The target and second capture probe can then be released from the first support and first capture probe. The first support and first capture probe can then be separated from the third medium presumably removing excess second capture probe nonspecifically bound to the first support which may cause noise in the assay.

Next, the target and second capture probe can be recaptured first by a fresh supply of first capture probe in the presence of detector probe and then by a first support. The first support and captured quaternary complex comprising a second target complex of the second capture probe:target:detector probe and bound first capture probe can be separated from the third medium and introduced to a fourth sample processing medium. Next, the second target complex can be released from the first support and first capture probe. These can be separated from the sample medium thereby removing excess detector probe nonspecifically bound to the first support and first capture probe and reducing background noise from the assay.

Next, one or more cycles of capture and release of the second target complex can be performed with the corresponding second support to further reduce background noise. Additionally, one or more cycles of capture and release using the first capture probe and first support can also be performed. The additional capture and release cycles may be performed in any order.

Finally, the second target complex is monitored for the presence or absence of detector probe indicating the presence or absence target in the original sample.

Those skilled in the art will appreciate that binding of probes to supports and target is facilitated by imposition of suitable binding conditions. Similarly, release of targets and probes from supports can be facilitated by imposition of releasing conditions. Binding and releasing conditions are well known in the art and include modulation of sample temperature and salt concentrations in sample solutions. Those skilled in the art will also appreciate that wash steps can be interposed between capture and release steps in both Dual Capture assay formats to further reduce background noise. Those skilled in the art will also appreciate that, capture probes are often added separately from the corresponding supports for the convenience of the assay to facilitate complex formation. However, capture probes and supports can be added together without otherwise disrupting the performance of the assay.

The Dual Capture methods of the invention are compatible with conventional sandwich assay procedures. The methods are compatible with a wide array of supports such as filters, dipsticks, and dispersible particles. The methods are compatible with conventional sandwich assay targets such as antigens and nucleic acid sequences, and their corresponding antibody and nucleic acid binding partners as probes. The methods are compatible with conventional labeling moieties and detection schemes.

The Dual Capture methods are particularly well-suited for nucleic acid hybridization assays. The methods apply equally well to assays for DNA and RNA targets. Nucleic acid probes and supports are readily constructed with the binding characteristics required for Dual Capture. For example, target specific nucleic acid sequences can be derivatized with one member of a ligand binding pair such as biotin. When used in conjunction with supports derivatized with the other member of the ligand binding pair, such as streptavidin for biotin, such probes will bind to both target and supports such that the binding is stronger to the supports than target. Thus conditions can be imposed whereby the probe will separate from the target but not the particles. Similarly, such probes and supports can be made by derivatizing target specific nucleic acid sequences with deazadeoxyguanosine residues and the corresponding supports with deoxycytidine residues. Those skilled in the art will appreciate that other probe-support combinations can be devised with the requisite properties.

Probes which bind more strongly to target than supports are well known and routinely used in conventional sandwich hybridization assays. For example, target specific nucleic acid sequences can be derivatized with homopolymeric tails of specific nucleotide residues such as deoxyadenylate residues dA. When used in conjunction with supports derivatized with deoxythymidine residues dT, such dA-tailed probes will bind to both target and dT derivatized supports such that the binding is stronger to the targets than the supports. Thus conditions can be imposed whereby the probe will separate from the support but not the target.

Nucleic acid hybridization assays are also compatible with supports which are dispersible within the sample media. Such supports are particularly advantageous because they enable rapid hybridization between capture probe and the support and, hence, a more rapid assay procedure. Examples of such supports are polystyrene beads and magnetic particles. Those skilled in the art will appreciate, however, that it may be difficult to capture and separate all of such supports from a sample medium. Nevertheless, those skilled in the art will be able to separate substantially all of such supports without compromising the assay.

The methods of the invention are amenable to use with kits. Such kits include supplies of first and second capture probes specific for the Class I or Class II method to be used. The kits also include a supply of detector probe. All probes are specific for the target to be detected. Additionally, the kits can include supplies of appropriate supports and reagents to facilitate binding, releasing and washing during the assay.

EXAMPLES

Materials

Paramagnetic particles derivatized with oligo $dT_{14}$ and $dC_{14}$ were prepared for use in the Examples as follows. Sub-micron ferric oxide particles (Advanced Magnetics, Inc., Cambridge, Mass.) were derivatized with $dT_{14}$ or $dC_{14}$ oligomers using the method described by Morrissey, Anal. Biochem., 181:345–349 (1989). The beads were blocked for 4 hrs. at 65° C. in Bead Blocking Buffer [100 mM Tris 4.9% BSA (Bovine Serum Albumin, Sigma Fraction 5, 0.5% Sarkosyl (Sigma), 10 mM EDTA, 0.05% Bronopol (Inolex, Philadelphia, Pa.), 0.01% antifoam [Dow-Corning FG-10], ph 7.8. The final suspension of particles was 0.25% (W/V) solids with a binding capacity of 300 pmol (deoxyadenylate) $dA_{50}$ per mg. Just before use, particles were separated from the buffer and made up to 0.045% in fresh Bead Blocking Buffer and Bead Blocking Buffer plus 4M guanidine hydrochloride (GuHCl).

Paramagnetic particles derivatized with streptavidin were obtained from Promega (Madison, Wisc). Purified 16S rRNA from Chlamydia trachomatis was used as the target in all examples. The 16S rRNA was purified using conventional techniques.

Various nucleic acid sequences are incorporated into the probes used in the Examples. These are The sequences 781 (Sequence ID No. 2) and 1660 (Sequence ID No. 3) were tailed with about 150 deoxyadenylate residue:; at the 3'end of each sequence to form probes dA-781 and dA-1660. This was accomplished by incubation with terminal deoxynucleotidyl transferase (Life Sciences, Inc.) following the method of Nelson et al, Methods in Enzymology, 68: 41–47, 1979. The sequence 3018 (Sequence ID No. 1) was also tailed with about 150 deazadeoxyguanosine residues (C7dG) at the 3'end of the sequence to form probe C7dG-3018. This was accomplished using the method described by Nelson et al.

The sequence C29 (Sequence ID No. 4) was used as the detector probe in all examples without further modification. The RNA sequence C29 (Sequence ID No. 4) was made from a DNA sequence complementary to C29 (Sequence ID No. 4) prepared by conventional methods. The complementary sequence was cloned into a transcriptase vector. C29 was transcribed from the cloned DNA using a $T_7$ RNA polymerase kit from Promega.

Examples 1–3 demonstrate matrix experiments illustrating various embodiments, features and advantages of the invention. For example, Example 1 provides a side by side comparison of the Class I Dual Capture Methodology of the invention with standard Reversible Target Capture Methodology. The example demonstrates the detection of targets using these assay methodologies and also the various components of noise generated during these assays for purposes of comparison. Example 1 demonstrates the noise generated during the assays attributable to nonspecific binding of detector probe to support and detector probe to capture probe.

Example 1. This example compares signal and noise from the Dual Capture Class I methodology of the invention with those from standard Reversible Target Capture methodology

| Sequence Ref. No. | Sequence (5' - 3') |
| --- | --- |
| 3018 (Sequence ID No. 1) | cCTTTAACGTTACTCGGATGCCCAAA |
| 781 (Sequence ID No. 2) | CTTTAACGTTACTCGGATGCCCAAATATCGCCACAT |
| 1660 (Sequence ID No. 3) | CTGCTGCCTCCCGTAGGAGTTTGGGCCGTGTCTC-AGTTCCAGTGT |
| C29 (Sequence ID No. 4) | GGGGACCCCCCCGGAAGGGGGGGACGAG-GUGCGGGCACCUCGUACGGGAGUUCGAC-CGUGACGCGUCGUCGAGUUGAGGCCUUU-ACCCCACCAACUAGCUGAUAUCAC-AUACUGAAUCUUUAGTCACGGGCU-AGCGCUUUCGCGCUCUCCCAGGUGACGC-CUCGUGAAGAGGCGUGACCUUCGUGCGU-UUCGGUAACGCACGAGAACCGCCACGCU-GCUUCGCAGCGUGGCCCCUUCGCGCAGC-CCGCUGCGCGAGGUGACCCCCCGAAGGG-GGGUUCCC |

The nucleic acid sequences 3018, 781, and 1660 were made using conventional betacyanoethyl phosphoramidite chemistry and conventional nucleic acid synthesizer equipment such as the 380-B Synthesizer from Applied Biosystems, Foster City, Calif. The sequences were modified for use as capture and detector probes as follows.

The sequence 3018 (Sequence ID No. 1) was biotinylated to form probe B-3018 by first modifying the 5'end of sequence 3018 (sequence ID No. 1) to contain a primary amine. This was accomplished by addition of an aminopropyl-modified cystidine phosphoramidite. Deprotection of the phosphates and nucleotide bases was accomplished by standard methods. The crude oligonucleotide mixtures were purified by reverse phase HPLC The amino-modified oligonucleotide was labeled with biotin using the Fluo Reporter Biotin Labeling Kit, F-2610 from Molecular Probes, Inc.

in the detection of Chlamydia trachomatis. The Dual Capture assays used B 3018 and dA-781 capture probes. The RTC assays used only the dA-781 capture probe. The assays were performed as follows.

Five solutions were prepared:

Solution 1 was made up to comprise 700 microliters of 1.4 * $10^6$ purified target molecules, 70 ng B-3018 capture probe, 1.4 * $10^{12}$ molecules of C29 detector probe in 4M guanidine hydrochloride (GuHCl), 125 mM Tris pH 7.8 and 16 mM EDTA.

Solution 2 was made up to comprise 700 microliters of 1.4 * $10^6$ purified target molecules, 70 ng dA-781 capture probe, 1.4 * $10^{12}$ molecules of C29 detector probe in 4M GuHCl, 125 mM Tris pH 7.8, 16 mM EDTA.

Solution 3 was made up to comprise 703 microliters of 1.4 * $10^{12}$ molecules of C29 detector probe in 4M GuHCl, 125 mM Tris pH 7.8, 16 mM EDTA.

Solution 4 was made up to comprise 1600 microliters of 160 ng B-3018 capture probe, $3.2 * 10^{12}$ molecules of C29 detector probe in 4M GuHCl, 125 mM Tris pH 7.8, 16 mM EDTA.

Solution 5 was made up to contain 1600 microliters of 160 ng dA-781 capture probe, $3.2 * 10_{12}$ molecules of C29 detector probe in 4M GuHCl, 125 mM Tris pH 7.8, 16 mM EDTA.

An 8(A-H)×12(1-12)96 well rack for 1.5 ml polypropylene tubes (Micronics, Flow Laboratories, McLean, Va.) was set up. Fifty microliter aliquots of solutions 1-5 were added to the tubes as follows:

50 μl ($10^5$ target molecules plus probes) Solution 1 was added to tubes A-B 1-6.

50 μl ($10^5$ target molecules plus probes) Solution 2 was added to tubes A-B 7-12.

50 μl Solution 3 was added to tubes C 1-12.

50 μl Solution 4 was added to tubes D-H 1-6.

50 μl Solution 5 was added to tubes D-H 7-12.

The content of the rack can be represented schematically as follows.

Rack setup:

All tubes were incubated for 30 min. at 37° C. to allow the Chlamydia target to hybridize to capture probe and detector probe. Following incubation, a 350 μl suspension of 0.023% streptavidin derivatized particles in Bead Blocking Buffer [4% BSA (Bovine Serum Albumin, Sigma Fraction 5), 0.5% Sarkosyl, 100 mM Tris, 20 mM EDTA, 0.01% antifoam], pH 8.0 was added to each of tubes A-H 1-6. A 1001 μl suspension of 0.045% $dT_{14}$ derivatized particles in Bead Blocking Buffer containing 4M GuHCl was added to each of tubes A-H 7-12. After mixing on a platform vortex, the tubes were incubated at 37° C. for 5 min. to capture the ternary capture probe: target: detector probe complexes. The particles and captured ternary complexes were collected at the sides of the tubes using a magnetic separations device as described in U.S. Pat. No. 4,988,618 to Li et al., which is incorporated herein by reference. The supernatants were aspirated away.

Next, the particles were washed to remove detector probe unbound to the target. Two hundred microliters of Wash Buffer [300 mM NaCl, 0.5% Sarkosyl, 100 mM Tris, 20 mM EDTA, 0.5% BSA, 0.1% antifoam], pH 8.1 was added to each tube. The tubes were mixed and incubated at 37° C. for 2 min. The particles and captured ternary complexes were collected at the sides of the tubes as described above. The supernatants were aspirated away. The particles were washed twice more in the same manner.

Next, 160 μl of Guanidine Thiocyanate (GuSCN) Buffer [2.5M GuSCN, 100 mM Tris, 10 mM EDTA, 0.5% Sarkosyl, and 0.5% BSA], pH 7.8 was added to each tube. After mixing, the tubes were incubated at 37° C. for 5 min. This resulted in release of the target:detector probe segment of the ternary complex in tubes A-H 1-6, and release of the capture probe: target:detector probe ternary complex in tubes A-H 7-12. The B-3018 capture probe remains bound to the streptavidin particles in tubes A-H 1-6. After 5 min. the particles were collected at the sides of the tubes using a magnetic separation device as described above. The supernatants were transferred to clean tubes.

Next, 40 μl of 500 ng/ml dA-781 capture probe in 10 mM Tris, 1 mM EDTA was added to each supernatant of tubes A-H 1-6. Forty microliters of 10 mM Tris and 1 mM EDTA was added to each supernatant of tubes A-H 7-12. The tubes were incubated for 30 min. at 37° C. to allow dA-781 capture probe to hybridize to the target: detector probe segment in tubes A-H 1-6. Three hundred microliters of 0.05% $dT_{14}$ particles in Bead Blocking Buffer was added to all tubes. The ternary complexes were captured on the $dT_{14}$ particles. The particles were collected at the sides; of the tubes as described above and the supernatants were aspirated away. The particles were then washed with Wash Buffer as described above to remove detector probe unbound to the target. The supernatant was aspirated away.

Next, the ternary complexes were released from the particles by addition 100 μl Release Buffer [25 mM NaCl, 100 mM Tris, 20mM EDTA, 0.2% Sarkasyl, 0.05% Bronopol and 0.05% BSA], pH 8.1 as described above. The supernatants with released ternary complexes were transferred to clean tubes.

Next, 200 μl of a suspension of 0.045% oligo $dT_{14}$ particles in Buffer A [4% BSA, 4M GuHCl, 100 mM Tris, 20 mM EDTA, 0.5% Sarkosyl, and 0.1% antifoam], pH 7.8 was added to each of the released supernatants. The ternary complexes were captured onto the particles as described above. The particles were collected at the sides of the tubes as described above and the supernatants were aspirated away.

The particles were then washed twice in pre-Amp Wash Buffer [300 mM KCl, 50 mM Tris, 1 mM EDTA], pH8.0. The supernatants were aspirated away. Next, 150 μl of Pre-Amp Release Buffer [50 mM Tris, 1 mM EDTA, 0.5% NP-40] was added to each tube. After mixing, the tubes were incubated at 37° C. This resulted in release of the ternary complexes. The particles were separated from the supernatants as described before.

The presence of target was determined by replicating the MDV-like C29 detector probes with Qβ-replicase in the presence of the intercalating dye propidium iodide and measuring the time required to produce a positive response. More particularly, 100 μl of the supernatant from each tube was added to a 100 μl mixture of 220 mM Tris pH 7.8, 40 mM $MgCl_2$, 600 μM each of the nucleotide triphosphates ATP, CTP, GTP and UTP (Pharmacia), 50 ng propidium iodide and 1 μg of purified Qβ-replicase (specific activity of 2,000 units/mg). The Qβ-replicase was obtained as described in U.S. Pat. No. 5,141,857 which is incorporated herein by reference. The tubes were capped and kept on ice until ready for measurement.

The 96 tubes were processed simultaneously. Each tube was maintained at 37° C.± 0.25° C. Each tube was excited at 510 nm and read at 610 nm every 40 sec. for a period of 45 min. The output fluorescence was analyzed numerically for response time. The response time was taken as the intersection of the fluorescent response with the baseline (no response). The intersection was determined using third order polynomials to fit the fluorescent response. The baseline was averaged. The response time represents a quantifiable determination of the presence of target as it is inversely proportional to the log of the number of template molecules present in the sample, Cahil et al., Clin. Chem. 37:1482–1485, 1991.

Figure 1:
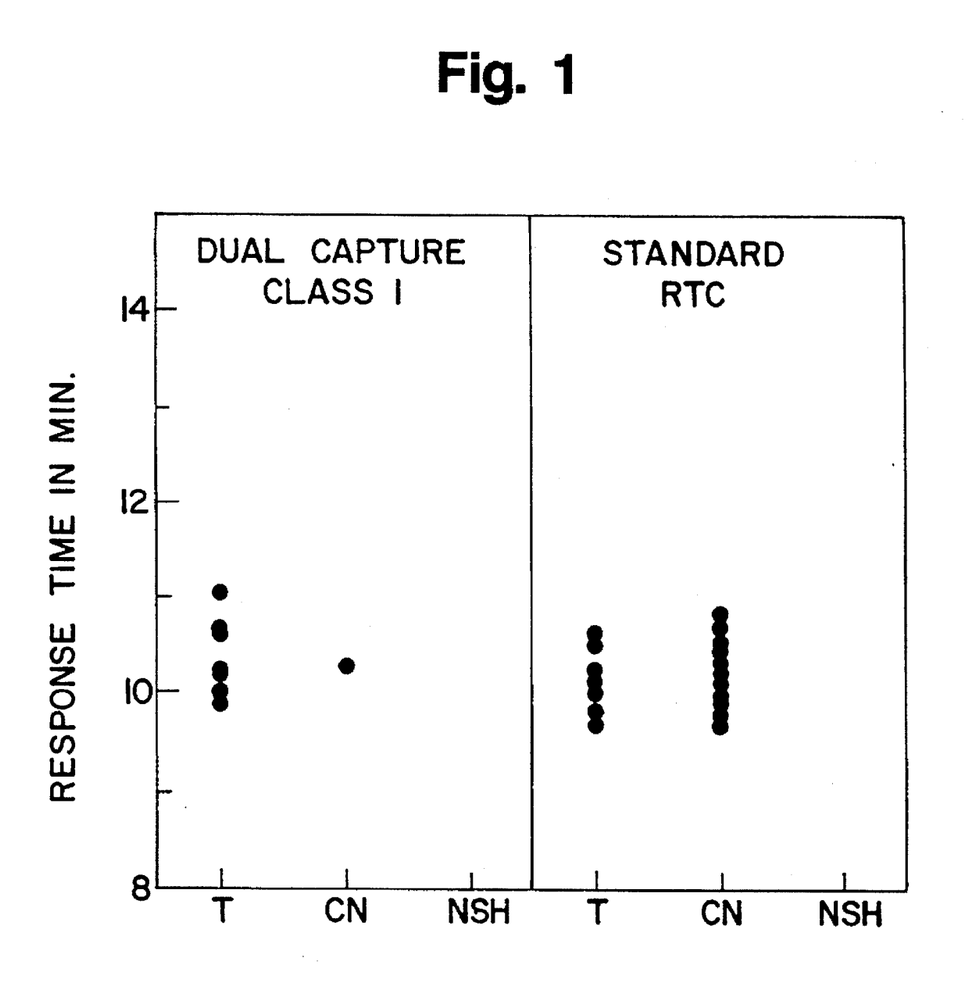
FIG. 1 presents side by side for comparison the results from a matrix of experiments demonstrating signal and noise production for nucleic acid hybridization assays for targets from Chlamydia trachomatis using the Dual Capture Class I methodology of the invention and standard Reversible Target Capture methodology.

FIG. 1 shows the cumulative results for each method. The Figure shows the responses generated by assays employing the Dual Capture format of the invention and the standard RTC format. In addition, FIG. 1 shows the time for responses generated by the assays in the presence of target (true signal) and in the absence of target (noise).

Ten of the 12 tubes for the Dual Capture method including target (A–B 1–6) were measured. All 10 produced a positive response. These are indicated by spots in the column above T. Eleven of the 12 tubes for the: standard RTC method including target (A–B 7–12) were measured. All 11 produced a positive response.

Twenty-three of the 30 tubes for the Dual Capture method including capture probes and detector probe but omitting target (D–H 1–6) were measured. Only 1 of the 23 produced a positive response. This is indicated by the spot in the column above CN. The response is attributable to the cyclable noise resulting from nonspecific binding of the C29 detector probe to the capture probes. Twenty-eight of the 30 tubes for the standard RTC method including capture probe and detector probe but omitting target (D–H 7–12) were measured. All 28 produced a positive response attributable to cyclable noise. All 6 of the 6 tubes for each assay method including C29 detector probe but excluding target and capture probe (Dual Capture: C 1–6; RTC: C 7–12) were measured. All 28 produced a positive response attributable to cyclable noise.

All 6 of the 6 tubes for each assay method including C29 detector probe but excluding target and capture probe (Dual Capture: C 1–6; RTC: C 7–12) were measured. Responses here would be attributable to nonspecific binding and/or hybridization of detector probe to the supports used in the assays. However, none of the tubes for either method produced a positive response. This is indicated by the absence of spots in the column above NSH.

The results depicted in FIG. 1 demonstrate the superiority of the Dual Capture Class I methodology of the invention over standard RTC methodology. As FIG. 1 demonstrates, both methodologies are able to detect the signal generated in the presence of target. Similarly, both methods are able to eliminate the background signal (noise) generated by nonspecific binding of detector probe to assay supports. However, the Dual Capture methodology is clearly superior in eliminating or substantially reducing the background signal resulting from cyclable noise. FIG. 1 demonstrates that such cyclable noise observed with the RTC method is competitive with the signal generated by the $10^5$ targets. Thus, the sensitivity of the assay is limited by the cyclable noise to about $10^5$ targets. In contrast, the cyclable noise produced in the Dual Capture assay is almost eliminated entirely and is clearly distinguishable from the signal produced by the $10^5$ targets. FIG. 1 demonstrates that the Dual Capture assay is much more sensitive than the standard RTC method.

EXAMPLE 2

This example compares signal and cyclable noise for separate embodiments of the Dual Capture Class I method in the detection of Chlamydia trachomatis. One set of assays was performed using B-3018 and dA-781 capture probes as in Example 1. The second set of assays was performed using C7dG-3018 and dA-781 capture probes. Both sets used the C29 detector probes. The assays were performed as follows.

Five solutions were prepared:

Solution 1 was made up to comprise 1400 μl of $1.4 * 10^6$ purified targets molecules, 140 ng B-3018 capture probe, $2.8 * 10^{12}$ molecules of C29 detector probe in 4M GuHCl, 125 mM Tris pH 7.8, 16 mM EDTA.

Solution 2 was made up to comprise 1400 μl of $1.4 * 10^6$ purified target molecules, 140 ng C7dG-3018 capture probe, $2.8 * 10^{12}$ molecules of C29 detector probe in 4M GuHCl, 125 mM Tris pH 7.8, 16 mM EDTA.

Solution 3 was made up to comprise 1400 μl of $2.8 * 10^{12}$ molecules of C29 detector probe in 4M GuHCl, 125 mM Tris pH 7.8, 16 mM EDTA.

Solution 4 was made up to comprise 3200 μl of 320 ng B-3018 capture probe, $6.4 * 10^{12}$ molecules of C29 detector probe in 4M GuHCl, 125mM Tris pH 7.8, 16 mM EDTA.

Solution 5 was made up to comprise 3200 μl of 320 ng C7dG-3018 capture probe $6.4 * 10^{12}$ molecules of C29 detector probe in 4M GuHCl, 125 MM Tris pH 7.8, 16 mM EDTA.

An 8 (A–H)×12(1–12) 96 well rack for 1.5 ml polypropylene tubes (Micronics, Flow Laboratories) was set up. One hundred microliter aliquots of solutions 1–5 were added to the tubes as follows:

100 μl ($10^5$ target molecules plus probes) Solution 1 was added to tubes A and B 1–6.

100 μl ($10^5$ target molecules plus probes) Solution 2 was added to tubes A and B 7–12.

100 μl Solution 3 was added to tubes C1–12.

100 μl Solution 4 was added to tubes D–H 1–6.

100 μl Solution 5 was added to tubes D–H 7–12.

Thus, the tubes A–H 1–6 demonstrate facets of the Dual Capture Method using B-3018 capture probe; tubes A–H 7–12 demonstrate facets of the method using C7dG-3018 capture probe.

All tubes were then incubated for 30 min. at 37° C. to allow the Chlamydia target to hybridize to capture probe and detector probe. Following incubation a 300 μl suspension of 0.027% streptavidin derivatized particles in Bead Blocking Buffer [4% BSA (Bovine Serum Albumin, Sigma Fraction 5), 0.5% Sarkosyl, 100 mM Tris, 20 mM EDTA, 0.01% antifoam], pH 8.0 was added to each of tubes A–H 1–6. A 200 μl suspension of 0.045% $d(C)_{14}$ derivatized particles in Bead Blocking Buffer containing 4M GuHCl was added to each of tubes A–H 7–12. After mixing, the tubes were incubated at 37° C. for 5 min. to capture the ternary capture probe: target: detector probe hybrids. The particles were then collected at the sides of the tubes using a magnetic separations device as described in U.S. Pat. No. 4,988,618. The supernatants were aspirated away.

Next, the particles in all tubes were washed to remove detector probe unbound to the target. Two hundred microliters of Low Salt Wash/Release Buffer [25 mM NaCl, 0.2% Sarkosyl, 25 mM Tris 5 mM EDTA, 0.05% BSA, 0.05% Bronopol], pH 8.1 was added to each tube. The tubes were then mixed on a platform vortex for 30 sec. and incubated at 37° C. for 2 min. The particles and captured hybrids were collected at the sides of the tubes using a magnetic separation device as described before. The supernatants were aspirated away. The particles were washed twice more in the same manner.

Next, 100 μl of Guanidine Thiocyanate (GuSCN) Buffer [2.5M GuSCN, 100 mM Tris, 10 mM EDTA, 0.5% Sarkosyl and C5% BSA], pH 7.8 was added to each tube. After mixing, the tubes were incubated for 5 min at 37° C. This resulted in release of the target: detector probe segment of the ternary complex since the B-3018 and C7dG-30185 capture probes dissociate from the target but not from the particles. After 5 min the particles were collected at the sides of the tubes using a magnetic separations device as described above. The supernatants were transferred to clean tubes.

Next, 50 μl of 300 ng/ml dA-781 capture probe in 10 mM EDTA was added to each supernatant. The tubes were incubated for 30 min. at 37° C. to allow the dA-781 capture probe to hybridize to the target: detector probe. Two hundred microliters of 0.05% $dT_{14}$ particles in Bead Blocking Buffer was molded to all tubes. The ternary complexes were captured on the $dT_{14}$ particles. The particles were then collected at the sides of the tubes as described above and the supernatants were aspirated away. The particles were then washed with High Salt Wash Buffer [300 mM NaCl, 0.5% Sarkosyl, 100 mM Tris, 20 mM EDTA, 0.5% BSA, 0.1% antifoam], pH 8.1 to remove detector probe unbound to the target.

Next, the ternary complexes were released into 100 μl/tube of Low Salt Wash/Release Buffer as described above. The released supernatants were transferred to clean tubes. To each tube was then added 200 μl of a suspension of $dT_{14}$ particles in Buffer A [4% BSA, 4M GuHCl, 100 mM Tris, 20 mM EDTA, 0.5% Sarkosyl, and 0.1% antifoam], pH 7.8. The ternary complexes were captured onto the particles as described above. The particles were collected at the sides of the tubes as described above and the supernatants were aspirated away.

The particles were then washed twice in the High Salt Wash Buffer. The ternary complexes were then released into 100 μl of the Low Salt Wash/Release Buffer. The released supernatants were transferred to clean tubes.

Next, 200 μl of a suspension of $dT_{14}$ particles in Buffer A was added to each supernatant and the ternary complexes were captured. The particles were collected at the sides of the tubes as before and the supernatants were aspirated away. The particles were then washed twice in Pre-Amp Buffer [300 μM KCl, 50 μlM Tris, 1 mM EDTA], pH 8.0 as described before. Finally, the ternary complexes were released into 150 μl Pre-Amp Release Buffer [50mM Tris, 1 mM EDTA and 0.5% NP-40]as described before. The particles were separated from the supernatants as described before.

Figure 2:
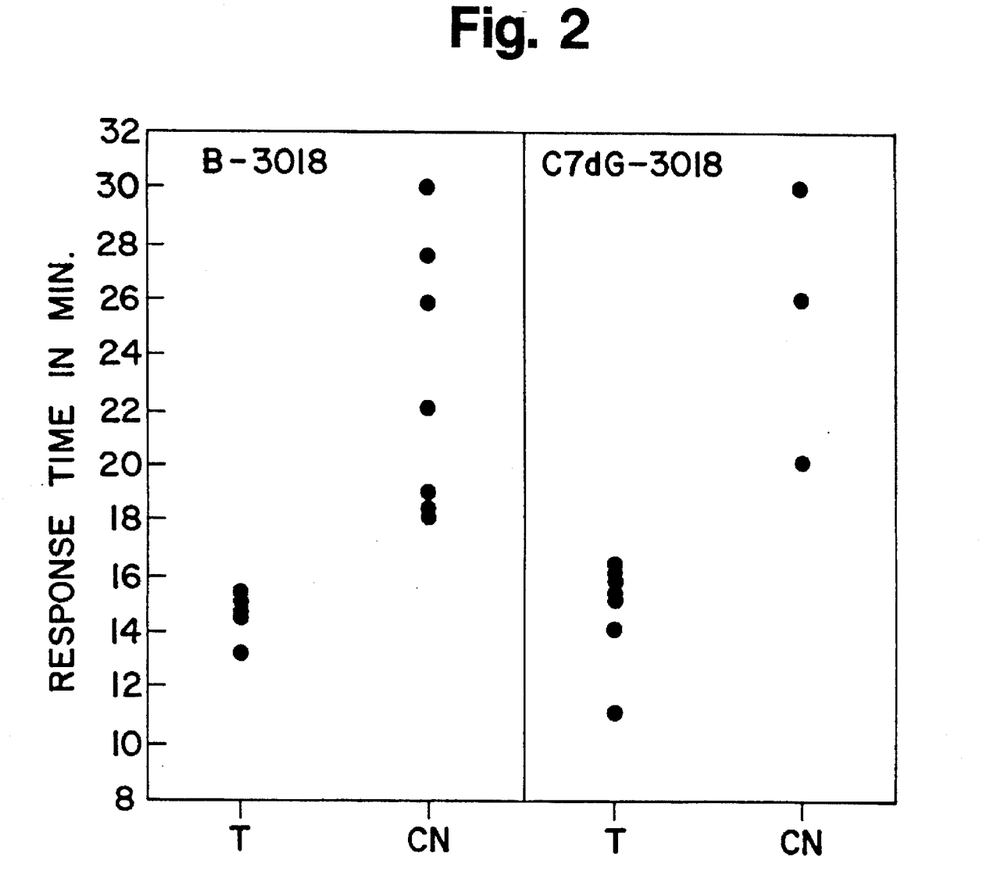
FIG. 2 presents side by side for comparison the results from a matrix of experiments demonstrating signal and noise production for nucleic acid hybridization assays for targets from Chlamydia trachomatis using separate embodiments of the Dual Capture Class I methodology of the invention.

The presence of target was determined as in Example 1. FIG. 2 shows the cumulative results for each method with respect to responses generated in the presence of target (column T) and by cyclable noise (column CN).

All 12 of the 12 tubes for each assay method including target, capture and detector probe (tubes A–B 1–6 using B-3018 capture probe and A–B 7–12 using C7dG-3018 capture probe) were measured. All tubes provided a positive response All of the tubes including capture, and detector probes but omitting target (D–H 1–6 for B-3018 capture probe, D–H 7–12 for C7dG-3018 capture probe) were measured. Only 7 of the 30 tubes using B-3018 capture probe produced a positive response. Only 3 of the 30 tubes using C7dG-3018 capture probe produced a positive response. These responses are attributable to cyclable noise.

The results in FIG. 2 demonstrate that the assays are comparable in ability to distinguish signal resulting from target relative to signal attributable to cyclable noise.

EXAMPLE 3

This example compares signal and noise from the Dual Capture Class II methodology of the invention with those from a comparable RTC method. The Dual Capture Class II assays used B-3018 and dA-1660 capture probes. These probes hybridize to exclusive sequences of the target Chlamydia trachomatis 16S rRNA. The nucleic acid sequence 1660 (Sequence ID No. 3) is a universal sequence to 16S eubacterial rRNA. The RTC assays used only dA-1660 capture probes. The assays were performed as follows.

Nine solutions were prepared as follows:

Solution 1 was made up to comprise 1100 μl of $1.1 * 10^7$ purified target molecules, 110 ng B-3018 capture probe and 110 ng dA-1660 capture probe in 4M GuHCl, 125 mM Tris pH 7.8, 16 mM EDTA.

Solution 2 was made up to comprise 1100 μl of $1.1 * 10^7$ purified target molecules and 110 ng dA-1660 capture probe in 4M GuHCl, 125 mM Tris, pH 7.8, 16 mM EDTA.

Solution 3 was made up to comprise 1100 μl of $1.1 * 10^6$ purified target molecules, 110 ng B-3018 capture probe and 110 ng dA-1660 capture probe in 4M GuHCl, 125 mM Tris pH 7.8, 16 mM EDTA.

Solution 4 was made up to comprise 1100 μl of $1.1 * 10^6$ purified target molecules and 5 110 ng dA-1660 capture probe 4M GuHCl, 125 mM Tris pH 7.8, 16 mM EDTA.

Solution 5 was made up to comprise 1600 μl of 160 ng B-3018 capture probe and 160 ng dA-1660 capture probe in 4M GuHCl, 125 mM Tris pH 7.8, 16 mM EDTA.

Solution 6 was made up to comprise 1600 μl of 160 ng dA-1660 capture probe in 4M GuHCl, 125 mM Tris pH 7.8, 16 mM EDTA.

Solution 7 was made up to comprise 1100 μl of 4 mM GuHCl, 125 mM Tris pH 7.8, 16 mM EDTA.

Solution 8 was made up to comprise 2500 µl of 750 ng B-3018 capture probe and 3.8 * $10^{12}$ molecules of C29 detector probe in 10 mM Tris 1 mM EDTA, pH 8.0.

Solution 9 was made up to comprise 2500 µl of 750 ng dA-781 capture probe and 3.8 * $10^{12}$ molecules of C29 detector probe in 10 mM Tris, 1 mM EDTA, pH 7.8.

Eight (A–H)×10(1–10) wells of an 8×12 96 well rack for 1.5 ml polypropylene tubes was set up. One hundred microliter aliquots of solutions 1–7 were added to the tubes as follows:

100 µl($10^6$ target molecules plus capture probes) Solution 1 was added to tubes A–B 1–5.

100 µl($10^6$ target molecules plus capture probes) Solution 2 was added to tubes A–B 6–10.

100 µl($10^5$ target molecules plus capture probes) Solution 3 was added to tubes C–D 1–5.

100 µl($10^5$ target molecules plus capture probes) Solution 4 was added to tubes C–D 6–20.

100 µl Solution 5 was added to tubes E–G 1–5.

100 µl Solution 6 was added to tubes E–G 6–10.

100 µl Solution 7 was added to tubes H 1–10.

All tubes were incubated for 30 min. at 37° C. to allow the Chlamydia target to hybridize to the capture probes. Following incubation, a 200 µl suspension of 0.045% d(T)$_{14}$ derivatized particles in Bead Blocking Buffer pH 7.8 containing 4M GuHCl was added to each tube. After mixing on a platform vortex, the tubes were incubated at 37° C. for 5 min. to capture the capture probe: target hybrids. The particles were collected at the sides of the tubes using a magnetic separations device as described previously. The supernatants were aspirated away.

Next, the particles were washed m remove capture probe unbound to the target. Two hundred microliters of High Salt Wash Buffer [300 mM NACl, 0.5% Sarkosyl, 100 mM Tris, 20 mM EDTA, 0.5% BSA, 0.1% antifoam], pH 8.1 was added to each tube. The tubes were mixed on a platform vortex and incubated at 37° C. for 2 min. The particles and captured hybrids were collected at the sides of the tubes using a magnetic separations device as described in U.S. Pat. No. 4,988,618. The supernatants were aspirated away. The particles and hybrids were washed again in the same High Salt Wash Buffer.

Next, 100 µl of Low Salt Wash/Release Buffer [25 mM NaCl, 0.2% Sarkosyl, 25 mM Tris, 5 mM EDTA, 0.5% BSA, 0.05% Bronopol], pH 8.1 was added to all tubes. After mixing, the tubes were incubated for 5 min. at 37° C. to release the target capture probe hybrids from the particles. The particles were collected at the sides of the tubes. The supernatants were transferred to new tubes.

Next, 100 µl of a suspension of 0.04% streptavidin derivatized paramagnetic particles in Bead Blocking Buffer also containing 1M GuHCl was added to each tube. After mixing, the tubes were incubated at 37° C. for 5 min. to recapture the target capture probe hybrids. The particles were then collected at the sides of the tubes and the supernatant was aspirated away. The particles and captured hybrid: were then washed once each with the High Salt Wash Buffer and Low Salt Wash Buffer to remove capture probe unbound to the target.

Next, 100 µl of Guanidine Thiocyante (GuSCN) Buffer [2.5M GuSCN, 100 mM Tris, 10 mM EDTA, 0.5% Sarkosyl, and 0.5% BSA], pH 7.8 was added to all tubes. After mixing, the tubes were incubated at 37° C. for 5 min. to release the target: dA-1660 capture probe hybrids. Under these conditions the B-3018 capture probe used in the Dual Capture Class II assays remain bound to the streptavidin particles.

The particles were then collected at the sides of the tubes as described before. The supernatants were transferred to clean tubes.

Next, 50 µl of Solution 8 (containing B-3018 capture probe and detector probe) was added to tubes A–H 1–5. Similarly, 50 µl of solution 9 (containing dA-781 capture probe and detector probe) was added to tubes A–H 6–10. The tubes were incubated for 30 min. at 37° C. to allow ternary capture probe: target: detector probe complexes to form.

Next, 150 µl of a suspension of 0.04% streptavidin derivatized particles in Bead Blocking Buffer was added to each of tubes A–H 1–5. Similarly, 300 µl of a suspension of 0.05% d(T)$_{14}$ derivatized particles in Bead Blocking Buffer was added to each of tubes A–H 6–10. The tubes were incubated at 37° C. for 5 min. to allow capture of the ternary complexes to the particles. The particles and captured ternary complexes were collected at the sides of the tubes as described before. The supernatants were then aspirated away. The particles were then washed with High Salt Wash Buffer as described to remove detector probe unbound to the target.

Next, 100 µl of 2.5M GuSCN Buffer was added to all tubes. After mixing, the tubes were incubated at 37° C. for 5 min. to release ternary complexes. More particularly, in tubes A–H 1–5 the ternary dA-1660 capture probe:target::detector probe complex is released into the Buffer while the B-3018 capture probe remains bound to the particles. In tubes A–H 6–10, the complex includes the two capture probes, target and detector probe. The particles were collected at the sides of the tubes and the supernatants were transferred to clean tubes.

Next, 200 µl of a suspension of 0.045% dT$_{14}$ particles in Bead Blocking Buffer was added to each supernatant. The complexes were captured onto the particles as described previously. The particles were collected at the sides of the tubes and the supernatants were aspirated away. The particles were washed twice in the High Salt Wash Buffer. The ternary complexes were then released in 100 µl of Low Salt Wash/Release Buffer. The supernatants ternary were transferred to clean tubes.

Next, 200 µl of a suspension of dT$_{14}$ particles in Buffer A was added to each supernatant. The complexes were recaptured onto the particles as described above. The particles were separated from the supernatant and washed twice in Pre-Amp Wash Buffer [300 mM KCl, 50 mM Tris, 1 mM EDTA], pH 8.0. The ternary capture probe: target: detector probe complexes were released into 150 µl Pre-Amp Release Buffer [50 mM Tris, 1 mM EDTA and 0.5% NP-40 as described previously. The particles were separated from the supernatants as described before.

Figure 3:
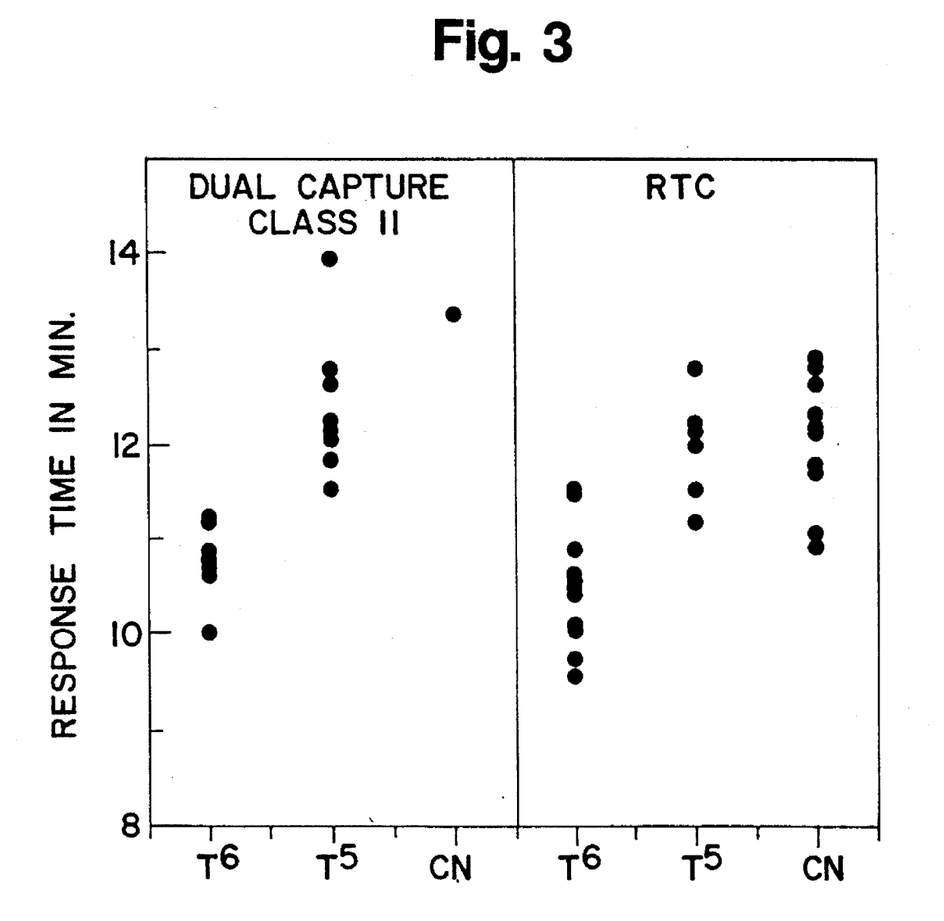
FIG. 3 presents side by side for comparison the results from a matrix of experiments demonstrating signal and noise production for nucleic acid hybridization assays for targets from Chlamydia trachomatis using the Dual Capture Class II methodology of the invention and a comparable Reversible Target Capture methodology.

The presence of target was determined as in Examples 1 and 2. FIG. 3 shows the cumulative results for each method with respect to responses generated in the presence of target for $10^6$ target molecules (A–B 1–10) and $10^5$ target molecules (C–D 1–10) and by cyclable noise (E–G 1–10) in the columns $T^6$, $T^5$ and CN, respectively.

All 10 of the 10 tubes for each Dual Capture Class II assay with target ($10^6$ and $10^5$ targets), capture and detector probes were measured. All tubes provided a positive response. All 10 tubes for the RTC assay method with $10^6$ targets, capture and detector probes were measured. All 10 provided a positive response. Nine of the 10 tubes for the RTC method with $10^5$ targets, capture and detector probes were measured. All 9 provided a positive response.

Fourteen of the 15 tubes including capture and detector probes but excluding target were measured for each assay method. Only 1 of the 14 tubes using the Dual Capture Class II method provided a positive response. In contrast, all 14 of the 14 tubes using the comparable RTC method provided a positive response. More importantly, this signal a attributable to cyclable noise is comparable to and indiscriminate from the true signal produced by $10^5$ targets. Accordingly, the sensitivity of the RTC method illustrated here is limited by cyclable noise. The sensitivity of the Dual Capture Class II method, however, is not so limited and easily exceeds $10^5$ targets.

---

Accordingly, that which is claimed is:

1. A method for assaying a sample for target nucleic acid comprising the steps of:
   (a) contacting the sample with a first capture probe and detector probe which first capture probe and detector probe each comprise a nucleic acid segment which in the presence of target nucleic acid bind to the target nucleic acid to form a first capture probe: target nucleic acid: detector probe ternary complex and wherein the detector probe is amplifiable by the enzyme Qβ replicase;
   (b) separating the first capture probe: target nucleic acid: detector probe ternary complex from the sample and introducing the ternary complex to a second medium;
   (c) separating the target nucleic acid: detector probe segment of the ternary complex from the first capture probe;
   (d) contacting the second medium with a second capture probe which comprises a nucleic acid which in the presence of target nucleic acid binds to the target nucleic acid to form a second capture probe: target nucleic acid; detector probe ternary complex;
   (e) separating the second capture probe: target nucleic acid: detector probe ternary complex from the second medium;
   (f) amplifying such detector probe as is present in the separated second capture probe: target nucleic acid: detector probe ternary complex with Qβ replicase; and
   (g) monitoring for the presence or absence of amplification of detector probe.

2. The method of claim 1 further comprising the steps of:
   (a) contacting the sample with a first support which binds to the first capture probe;
   (b) separating the first support and bound capture probe: target nucleic acid: detector probe ternary complex from the sample and introducing the support and bound capture probe: target nucleic acid: detector probe ternary complex into the second medium;
   (c) separating the target nucleic acid: detector probe segment of the ternary complex from the first support and bound capture probe;
   (d) contacting the second medium with the second capture probe which in the presence of target nucleic acid binds to the target nucleic acid to form the second capture probe: target nucleic acid: detector probe ternary complex and a second support which binds to the second capture probe;
   (e) separating the second support and bound second capture probe: target nucleic acid: detector probe ternary complex from the second medium and introducing them to a third medium;
   (f) separating the second support from the second capture probe: target nucleic acid: detector probe complex.

3. The method of claim 1 wherein one or more dispersible supports are used.

4. The method of claim 2 further comprising one or more cycles of the steps comprising:
   (a) contacting the medium containing the second capture probe: target nucleic acid: detector probe ternary complex with a new support wherein the new support binds to the second capture probe;
   (b) separating the new support and bound second capture probe: target nucleic acid: detector probe ternary complex from the medium containing the second capture probe: target nucleic acid: detector probe ternary complex;
   (c) introducing the new support and bound second capture probe: target nucleic acid: detector probe ternary complex into a new medium and releasing the second capture probe: target nucleic acid: detector probe ternary complex from the new support; and
   (d) separating the new support from the new medium.

5. The method of claim 4 wherein the target is a polynucleotide.

6. The method of claim 4 wherein the supports are dispersible.

7. A method for assaying a sample for target nucleic acid comprising the steps of:
   (a) contacting the sample with a first capture probe and a second capture probe which first and second capture probe each comprise a nucleic acid segment which in the presence of target nucleic acid bind to the target nucleic acid to form a target complex;
   (b) contacting the sample with a second support which binds to the second capture probe;
   (c) separating the second support and bound target complex from the sample and introducing the second support and bound target complex into a second medium;
   (d) separating the target complex from the second support and separating the second support from the second medium;
   (e) contacting the second medium with a first support which binds to the first capture probe;
   (f) separating the first support and bound target complex from the second medium and introducing the first support and bound target complex into a third medium;
   (g) separating the second capture probe: target nucleic acid segment of the target complex from the first support and first capture probe and separating the first support and first capture probe from the third medium;
   (h) contacting the third medium with fresh first capture probe and detector probe which is amplifiable by the enzyme Qβ replicase and comprises a nucleic acid segment which in the presence of target nucleic acid binds to the target nucleic acid forming a quaternary complex of first capture probe, second capture probe and detector probe bound to target nucleic acid;

(i) contacting the third medium with fresh first support which binds with the first capture probe;

(j) separating the first support and bound quaternary complex from the third medium and introducing the first support and bound quaternary complex into a fourth medium;

(k) separating the first support and bound first capture probe from the second capture probe: target nucleic acid: detector probe complex and separating the first support and bound first capture probe from the fourth medium;

(l) amplifying such detector probe as is present in the second capture probe: target nucleic acid: detector probe complex with Qβ replicase; and (m) monitoring for the presence or absence of amplified detector probe.

8. The method of claim 7 further comprising one or more cycles of the steps comprising:

(a) contacting the medium containing the second capture probe: target nucleic acid: detector probe complex with new support which binds to the second capture probe;

(b) separating the new support and bound second capture probe: target nucleic acid: detector probe complex from the medium containing the second capture probe: target nucleic acid: detector probe complex;

(c) introducing the new support and bound second capture probe: target nucleic acid: detector probe complex into a new medium and separating the second capture probe: target nucleic acid: detector probe complex from the new support; and (d) separating the new support from the medium containing the second capture probe: target nucleic acid: detector probe complex.

9. The method of claim 7 wherein the supports are dispersible.

* * * * *